US008889188B2

(12) United States Patent
Fang

(10) Patent No.: US 8,889,188 B2
(45) Date of Patent: Nov. 18, 2014

(54) LUMINESCENT CONDUCTING NANO-DRUG CRYSTAL ULTRA-THIN FILM SELF-ASSEMBLY AND USES

(75) Inventor: Yan Fang, Shanghai (CN)

(73) Assignee: Zhongshan Hospital, Fudan University, Shanghai (CN)

( * ) Notice: Subject to any disclaimer, the term of this patent is extended or adjusted under 35 U.S.C. 154(b) by 2068 days.

(21) Appl. No.: 11/813,265

(22) PCT Filed: Dec. 29, 2005

(86) PCT No.: PCT/CN2005/002368
§ 371 (c)(1),
(2), (4) Date: May 18, 2008

(87) PCT Pub. No.: WO2006/069542
PCT Pub. Date: Jul. 6, 2006

(65) Prior Publication Data
US 2010/0034884 A1 Feb. 11, 2010

(30) Foreign Application Priority Data

Dec. 31, 2004 (CN) .................. 2004 1 0099386

(51) Int. Cl.
*A61K 9/14* (2006.01)
*A61K 38/44* (2006.01)
*A61K 9/51* (2006.01)
*A61K 31/137* (2006.01)
*A61K 31/52* (2006.01)
*A61K 45/06* (2006.01)

(52) U.S. Cl.
CPC .................. *A61K 38/446* (2013.01); *A61K 9/51* (2013.01); *A61K 31/137* (2013.01); *A61K 31/52* (2013.01); *A61K 45/06* (2013.01); *A61K 9/14* (2013.01); *Y10S 977/775* (2013.01)
USPC .......................... 424/489; 424/94.4; 977/775

(58) Field of Classification Search
CPC ....... A61K 38/446; A61K 45/06; A61K 9/14; A61K 9/51; A61K 9/1694; A61K 38/44; B82Y 30/00
USPC .................................. 424/489, 94.4; 977/775
See application file for complete search history.

(56) References Cited

U.S. PATENT DOCUMENTS

| | | | |
|---|---|---|---|
| 5,589,692 A | | 12/1996 | Reed |
| 6,060,327 A | * | 5/2000 | Keen .................................. 506/9 |
| 2006/0292081 A1 | * | 12/2006 | Morton et al. ................... 424/46 |

FOREIGN PATENT DOCUMENTS

| | | | | |
|---|---|---|---|---|
| CN | 1079399 | | * 12/1993 | ............. A61K 37/50 |
| CN | 1079399 A | | 12/1993 | |

(Continued)

OTHER PUBLICATIONS

Yu et al. "Self-Assembly Techniques for Fabrications of Nanocomposite Thin Films." Wuhan Ligong Daxue Xuebao o Xinxi Yu Guangligongcheng Ban, 24(4), 2002, p. 137-141. English translation pp. 1-19.*

(Continued)

*Primary Examiner* — Aradhana Sasan
(74) *Attorney, Agent, or Firm* — Hamre, Schumann, Mueller & Larson, P.C.

(57) ABSTRACT

This invention involves two fields of photoelectron information materials and pharmaceuticals, especially refers to the self-assembly of conducting photoluminescence nanomedicine crystals and thin films and their preparation processes. In the invention, self-assembling unitary, binary, ternary and quaternary complexes of an antioxidase antioxidant, an agonist of the β-adrenergic receptors, an agonist of the $P_2$-purinergic receptors and an antagonist of benzalkonium-typed calcium channels is to employ an interaction of inelastic electron tunneling, which possesses photoelectron properties of inelastic electron tunneling and photoluminescence with the central wavelength ~500 nm and the wavelength wide ~200 nm in the size-controlled square or cubic geometrical complexes. The invention is not only beneficial for drug discovery targeted disease mechanisms, but also profitable for inventions of photoelectron sensing new materials.

20 Claims, 8 Drawing Sheets

(56) References Cited

FOREIGN PATENT DOCUMENTS

| | | | |
|---|---|---|---|
| CN | 2004/00099386.2 | * 12/2004 | ............. A61K 38/44 |
| DE | 19852543 | 5/2005 | |
| JP | 2003-076036 | 3/2003 | |

OTHER PUBLICATIONS

International Search Report of International Application No. PCT/CN2005/002368, Apr. 13, 2006.

Fang et al. "The mechanics of synergy of four drugs in protecting cortico-cerebral function from anoxic damage." Zhongguo Yingyong Shenglixue Zazhi, 12(3), 1996, p. 223-226.

Yu et al. "Self-Assembly Techniques for Fabrications of Nanocomposite Thin Films." Wuhan Ligong Daxue Xuebao • Xinxi Yu Guangligongcheng Ban, 24(4), 2002, p. 137-141.

Substitute Specification filed with Co-Pending U.S. Appl. No. 11/886,490 on Sep. 17, 2007.

Co-Pending U.S. Appl. No. 12/002,888, filed Dec. 19, 2007.

Co-Pending U.S. Appl. No. 12/008,904, filed Jan. 15, 2008.

Fang et al. Mode-actions of the Na(+)-Ca2+ exchanger: from genes to mechanisms to a new strategy in brain disorders. Biomed Pharmacother 52(4), 1998, p. 145-156 (Abstract Only).

* cited by examiner

_US 8,889,188 B2_

LUMINESCENT CONDUCTING NANO-DRUG CRYSTAL ULTRA-THIN FILM SELF-ASSEMBLY AND USES

RELATED APPLICATIONS

This application is the 35 U.S.C. §371 National Application of International Application No. PCT/CN05/002368, filed Dec. 29, 2005, which designated the United States, claiming priority to China Patent Application No. 200410099386.2, filed Dec. 31, 2004.

TECHNICAL FIELD

This invention relates to preparation and uses of luminescent conducting nanometer co-crystals of liquid pharmaceutical ingredients.

BACKGROUND

Protection from hypoxic injuries that cause cardiopulmonary and cerebral dysfunction is a focus of current clinical research. A decline in β-adrenergic receptors and $P_2$-purinergic receptors in cardiopulmonary and cerebral vascular systems, superoxide anion-induced endothelial injuries, and elevated intracellular calcium influx are key factors leading to cardiopulmonary and cerebral injuries. Pharmacotherapies using verapamil, isoprenaline, or superoxide dismutase alone for targeting the key loops of cardiopulmonary and cerebral hypoxic injuries have demonstrated low efficacy and high toxicity.

SUMMARY

In one aspect of the invention, self-assembled conducting photoluminescent compositions include complexes selected from the group consisting of unitary, binary, ternary, and quaternary complexes of a β-adrenergic agonist, a $P_2$-purinergic agonist, a phenylalkylamine calcium channel blocker, and an antioxidase antioxidant. The compositions are selected from the group consisting of nanomedicine crystals, ultra thin films, and combinations thereof. The nanomedicine crystals and the ultra thin films demonstrate inelastic electron tunneling.

The invention may include the following features. The β-adrenergic agonist may include isoprenaline. Concentration of the isoprenaline may be in a range of about 15.1 pM to about 2.0 µM. The $P_2$-purinergic agonist may include adenosine triphosphate. Concentration of the adenosine triphosphate may be in a range of about 1.0 nM to about 2.5 M. The phenylalkylamine calcium channel blocker may include verapamil. The concentration of verapamil may be in a range of about 2.0 nM to about 59.1 µM. The antioxidase antioxidant may include superoxide dismutase. The concentration of superoxide dismutase may be in a range of about 15.1 pM to about 151 pM.

Unitary complexes of a self-assembled conducting photoluminescent composition comprise a molar ratio of (phenylalkylamine calcium channel blocker:β-adrenergic agonist:antioxidase antioxidant:$P_2$-purinergic agonist) selected from the group consisting (i) 1:0:0:0; (ii) 0:1:0:0; (iii) 0:0:1:0; (iv) 0:0:0:1, and combinations thereof, in an $L_{16}(2)^{15}$ orthogonal design protocol. Binary complexes of a self-assembled conducting photoluminescent composition comprise a molar ratio of (phenylalkylamine calcium channel blocker:β-adrenergic agonist:antioxidase antioxidant:$P_2$-purinergic agonist) selected from the group consisting of (i) 1:1:0:0; (ii) 1:0:1:0; (iii) 1:0:0:1; (iv) 0:1:1:0; (v) 0:1:0:1; (vi) 0:0:1:1, and combinations thereof, in an $L_{16}(2)^{15}$ orthogonal design protocol. Ternary complexes of a self-assembled conducting photoluminescent composition comprise a molar ratio of (phenylalkylamine calcium channel blocker:β-adrenergic agonist:antioxidase antioxidant:$P_2$-purinergic agonist) selected from the group consisting of (i) 1:1:1:0; (ii) 1:0:1:1; (iii) 1:1:0:1; (iv) 0:1:1:1, and combinations thereof in an $L_{16}(2)^{15}$ orthogonal design protocol. Quaternary complexes of a self-assembled conducting photoluminescent composition comprise a molar ratio of (phenylalkylamine calcium channel blocker:β-adrenergic agonist:antioxidase antioxidant:$P_2$-purinergic agonist) selected from the group consisting of (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; (ix) 3:3:2:1, and combinations thereof, in an $L_9(3)^4$ orthogonal design protocol.

The self-assembled conducting photoluminescent nanomedicine crystals and ultra thin films may be prepared by a unitary, binary, ternary, or quaternary process comprising the steps of: (a) preparing a solution of verapamil hydrochloride, a solution of isoprenaline hydrochloride, a physiological buffer solution of superoxide dismutase, and a physiological buffer solution of adenosine triphosphate; (b) mixing a selected molar ratio of the solutions chosen according to $L_{16}(2)^{15}$ and $L_9(3)^4$ test protocols in physiological buffer solution; (c) dropping the mixture on a substrate to form a droplet of the mixture on the substrate; and (d) cooling the mixture on the substrate to −4° C. to form size-controlled self-assembled conducting photoluminescent nanomedicine crystals, conducting photoluminescent ultra thin films, or both.

In another aspect of the invention, a crystallized nanomedicine composition with luminescent and conducting properties includes one or more ingredients selected from the group consisting of: (a) a β-adrenergic receptor agonist; (b) a $P_2$-purinergic receptor agonist; (c) a phenylalkylamine calcium channel blocker; and (d) an antioxidase antioxidant.

The invention may include the following features. The nanomedicine composition is self-assembled on a substrate. The β-adrenergic receptor agonist may include isoprenaline. The $P_2$-purinergic receptor agonist may include adenosine triphosphate. The phenylalkylamine calcium channel blocker may include verapamil. The antioxidase antioxidant may include superoxide dismutase. The nanomedicine composition is selected from the group consisting of unitary, binary, ternary, and quaternary complexes.

The binary complexes of the nanomedicine composition may be selected from the group of molar ratios of (phenylalkylamine calcium channel blocker:β-adrenergic agonist:antioxidase antioxidant:$P_2$-purinergic agonist) consisting of (i) 1:1:0:0; (ii) 1:0:1:0; (iii) 1:0:0:1; (iv) 0:1:1:0; (v) 0:1:0:1; and (vi) 0:0:1:1. The ternary complexes of the nanomedicine composition may be selected from the group of molar ratios of (phenylalkylamine calcium channel blocker:β-adrenergic agonist:antioxidase antioxidant:$P_2$-purinergic agonist) consisting of (i) 1:1:1:0; (ii) 1:1:0:1; (iii) 1:0:1:1; and (iv) 0:1:1:1. The quaternary complexes of the nanomedicine composition may be selected from the group of molar ratios of (phenylalkylamine calcium channel blocker:β-adrenergic agonist:antioxidase antioxidant:$P_2$-purinergic agonist) consisting of (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and (ix) 3:3:2:1.

In another aspect of the invention, a method of making a self-assembled nanomedicine crystal or ultra thin film includes the steps of (a) forming a droplet of a solution comprising one or more ingredients selected from the group consisting of verapamil, isoprenaline, superoxide dismutase, and adenosine triphosphate on a substrate; (b) cooling the substrate to a temperature of about −4° C.; and (c) allowing the droplet to cool such that the ingredients in the droplet undergo a phase transition and self-assemble to form a crystal or an ultra thin film. A concentration of the verapamil when present in the solution may be in a range from about 2 nM to about 59.1 µM. A concentration of the isprenaline when present in the solution may be in a range from about 15 pM to about 2 µM. A concentration of the adenosine triphosphate when present in the solution may be in a range from about 1 nM to about 2.5 M, and a concentration of the superoxide dismutase when present in the solution may be in a range from about 15.1 pM to about 151 pM.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
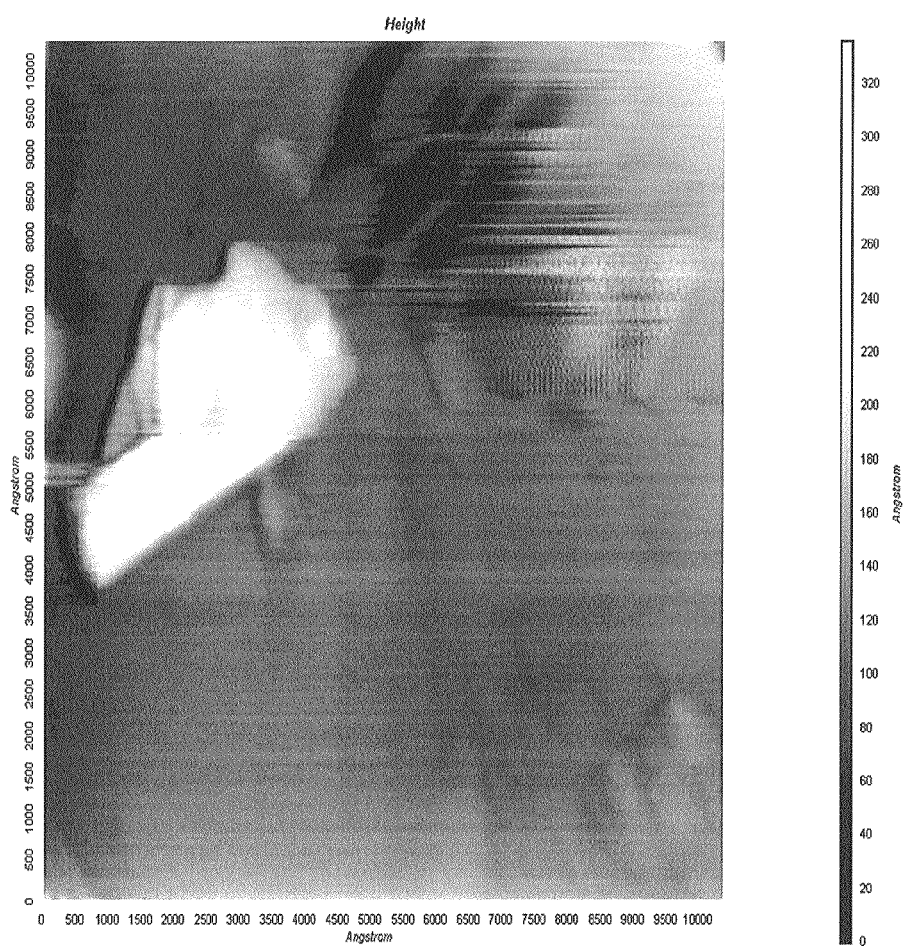
FIG. 1 is a conducting atomic force microscopy image (C-AFM) of the topographic structure of small, ternary self-assembled units (less than 10 nm) on a graphite substrate, as described in Example 3. The geometrical size is a molecular crystal thin film with a length of 400 nm, a width of 400 nm, and a height of 32 nm.

Self-assembled conducting photoluminescent nanomedicine crystals including unitary, binary, ternary, and quaternary complexes described herein demonstrate inelastic electron tunneling. The complexes include bottom-up, self-assembled unitary, binary, ternary, and quaternary co-crystallized complexes of an antioxidase antioxidant, agonists of β-adrenergic and $P_2$ purinergic receptors, and/or a phenylalkylamine (benzalkonium) calcium channel blocker.

Advantageous compositions of self-assembled conducting photoluminescent nanomedicine crystals and thin films with regular geometry include isoprenaline in a range of about 15 pM to about 2.0 µM adenosine triphosphate in a range of about 1.0 nM to about 2.5 M, verapamil in a range of about 2.0 nM to about 59.1 µM, and/or superoxide dismutase in a range of about 15.1 pM to about 151 pM. This liquid composition targets key loops of hypoxia-mediated cardiopulmonary and cerebral functional disorders, including the decline in β-adrenergic and $P_2$-purinergic receptors of cardiopulmonary and cerebral vascular endothelia, superoxide anion induced endothelial injuries, and an elevated intracellular calcium influx.

This preparation process employs an interaction of electron tunneling to self-assemble unitary, binary, ternary, and quaternary nanomedicine crystals from droplets of isoprenaline, verapamil, dismutase, and/or adenosine triphosphate. The mechanism-based drug design and spatial geometrical self-assembly method are advantageous for nano-drug discovery as well as photoelectron sensing materials.

The conducting property of the nanomedicine crystals is presented by current-potential (I-V) curves and their first and second derivatives. Inelastic electron tunneling interactions can be recognized by non-zero values in the $2^{nd}$ derivative of I-V curves in the nanomedicine crystals and ultra thin films. The energy loss range of self-assembled nanomedicine crystals and ultra thin films ranges from µeV to meV and eV. The photoluminescence of the self-assembled nanomedicine crystals and ultra thin films is expressed by photon absorption in laser micro-photoluminescence spectra.

The invention employs $L_{16}(2)^{15}$ and $L_9(3)^4$ orthogonal optimization methods, scanning probe microscopy (conducting atomic force microscopy), and/or low temperature laser micro-photoluminescence (PL) optical spectra and ORIGIN mathematical analyses (available from OriginLab Co., Northampton, Mass.). A key composition of this invention is the optimum self-assembly of unitary, binary, ternary, and quaternary elements of isoprenaline (β-adrenergic agonist), adenosine triphosphate ($P_2$-purinergic agonist), verapamil (phenylalkylamine calcium channel blocker), and superoxide dismutase (antioxidase antioxidant), respectively.

Unitary nanomedicine crystals and/or ultra thin films are respectively self-assembled according to (i) 1:0:0:0; (ii) 0:1:0:0; (iii) 0:0:1:0; and/or (iv) 0:0:0:1 complex preparation processes.

Binary nanomedicine crystals and/or ultra thin films are fabricated according to (i) 1:1:0:0; (ii) 1:0:1:0; (iii) 1:0:0:1; (iv) 0:1:1:0; (v) 0:1:0:1 and/or (vi) 0:0:1:1 complex preparation processes.

Ternary nanomedicine crystals and/or ultra thin films are synthesized according to (i) 1:1:1:0; (ii) 1:0:1:1; (iii) 1:1:0:1; and/or (iv) 0:1:1:1 complex preparation processes.

Quaternary nanomedicine crystals and/or ultra thin films are respectively manufactured according to (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and/or (ix) 3:3:2:1 complex preparation processes.

The I-V curves, their first and second derivatives, and energy spectra in the time and frequency domains of self-assembled unitary, binary, ternary, and quaternary complexes of this invention can generate 24 arrays of data and 24 sizes of different cubic nanomedicine crystals and/or ultra thin films. The three-dimensional size may be identified by C-AFM images, as shown in FIGS. 1-6. The smallest crystal sizes may range from angstroms to a length of 4.5 nm, a width of 4.5 nm, and a height of 0.1 nm. A thickness of the thinnest ultra thin films may range from 2.5 nm to 2 angstroms.

Figure 10:
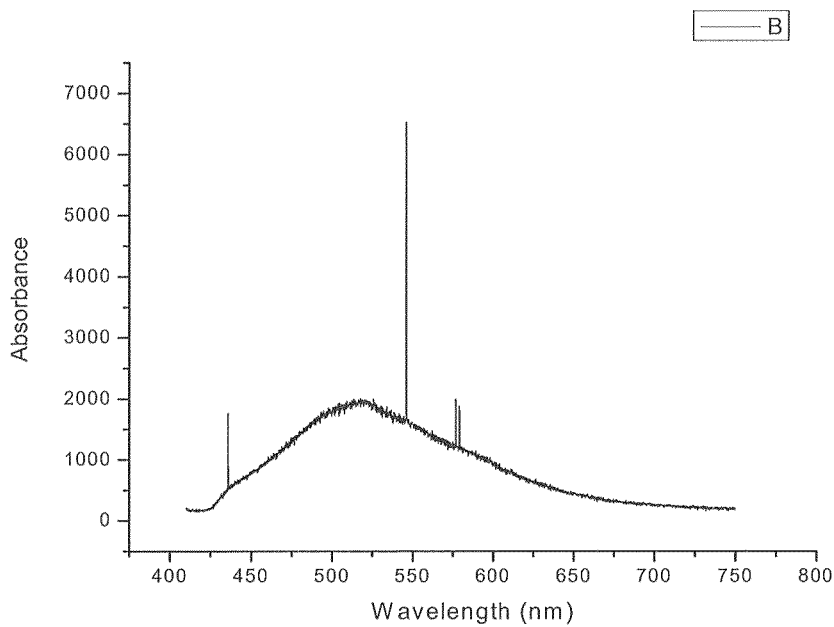
FIG. 10 is a time-resolved laser micro-luminescence spectrum indicating photoluminescence of the condensate in FIG. 6. The maximum photoluminescence intensity is 2000 absorbance units, and the photoluminescence bandwidth covers 450-750 nm. The central photoluminescence peak is located around 550 nm after automatic subtraction of the background signal, indicating the luminescence of the self-assembled nanometer crystal.

The self-assembled conducting photoluminescent nanomedicine crystals and ultra thin films possess square or cubic geometrical regular shape, controllable size, and inelastic electron tunneling and photoluminescence properties, as shown in FIGS. 1-10. Inelastic tunneling may be identified by the non-zero value in FIG. 9 that is the $2^{nd}$ derivative spectrum of FIG. 7. A low power feature of 1-8 μeV can be identified in FIG. 8. The central wavelength of the photon absorption spectrum is around 500 nm, with a bandwidth of about 200 nm, as shown in FIG. 10. This invention is advantageous in mechanism-aimed drug discovery as well as new photoelectron sensing materials.

The preparation processes of self-assembled conducting photoluminescent nanomedicine crystals and ultra thin films are stated as follows: Pharmaceutical liquids are prepared according to pharmaceutical standards issued by the Ministry of Health in China. Pharmaceutical liquids of verapamil hydrochloride, pharmaceutical liquids of isoprenaline hydrochloride, physiological buffer solutions of superoxide dismutase, and pharmaceutical liquids of adenosine triphosphate are prepared in the desired concentrations and mixed in a given volume or 1 mL buffer solution at room temperature then saved at −4° C. for applications. The self-assembled pharmaceuticals are dropped on graphite substrates and silicon chips according to $L_{16}(2)^{15}$ and $L_9(3)^4$ test design and saved at −4° C. for 12 hours, during which time the pharmaceutical liquids undergo a phase transition from a liquid phase to a solid phase.

In the $L_{16}(2)^{15}$ test design, there are four independent unitary groups, six independent binary groups, four independent ternary groups, one independent quaternary group, and a blank control group. In the $L_9(3)^4$ test design, there are nine quaternary groups at three molar ratios.

Example 1

Figure 3:
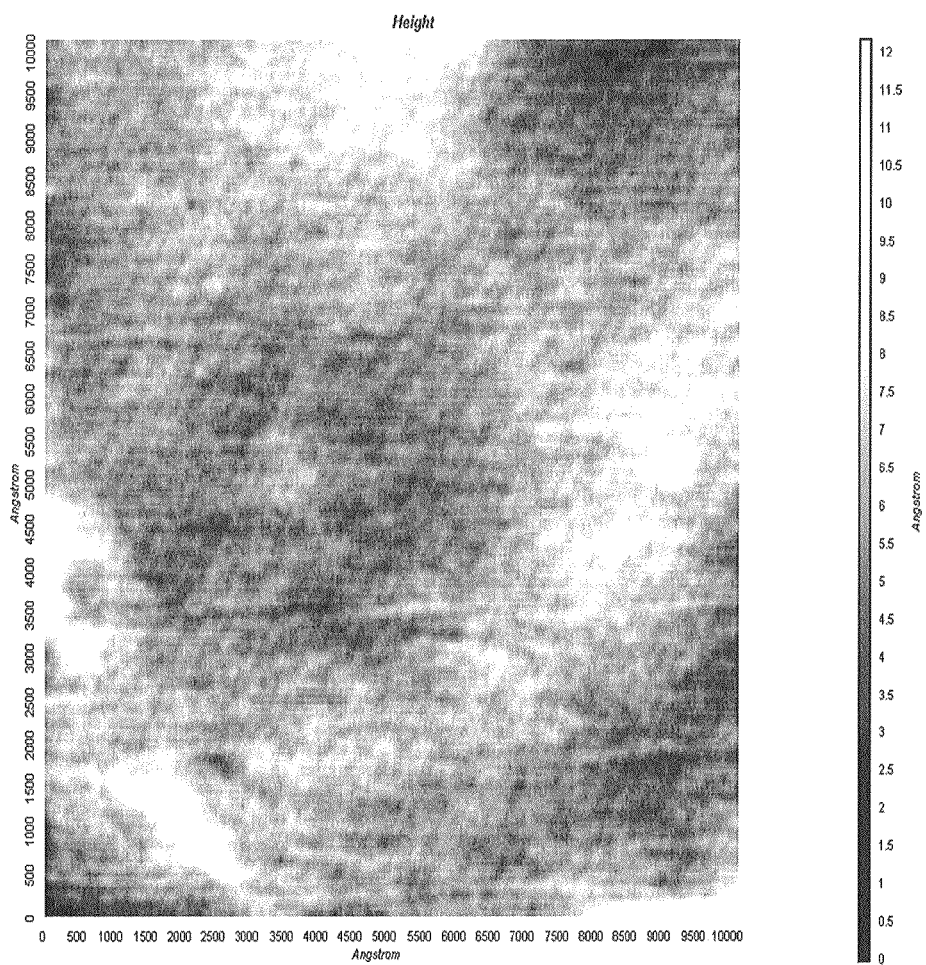
FIG. 3 is a conducting atomic force microscopy (C-AFM) image of the topographic structure of small, quaternary self-assembled quaternary units (less than 10 nm) on a silicon substrate, as described in Example 1. The geometrical size is a tilted cross-bar-like architecture crystal thin film with a length of 1000 nm, a width of 1000 nm, and a height of 1.2 nm. Net height is 0.3 nm, as deduced by the light/dark portions of the substrate.
Figure 4:
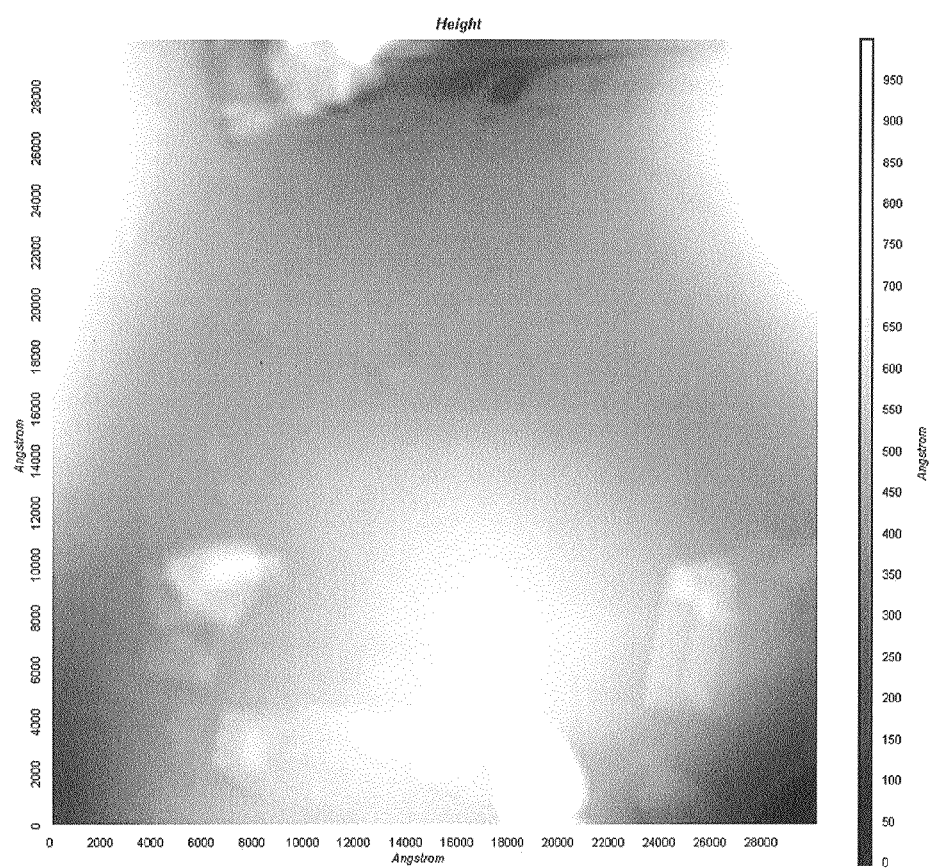
FIG. 4 is a conducting atomic force microscopy (C-AFM) image of the topographic structure of small, unitary (1:0:0:0) self-assembled units (unit length 0.34 nm) on a graphite substrate. The large crystals are non-symmetrical with a length and width of more than 1000 nm and a height of 95 nm.

Pharmaceutical liquids are prepared according to the pharmaceutical standards issued by the Ministry of Health in China. FIG. 3 is a C-AFM image of the 1:3:3:3 product obtained from Example 1.
i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. The pharmaceutical liquids are mixed in a molar ratio of 1:3:3:3 (verapamil:isoprenaline:superoxide dismutase:adenosine triphosphate) in 1 mL physiological buffer at room temperature. The solution is saved at −4° C. for application.
vi. 5 μL drops of the pharmaceutical liquid mixture are dropped on the graphite and silicon substrates according to the $L_9(3)^4$ test design, and saved at −4° C. for 12 hours to form size-controllable self-assembled nanomedicine crystals and/or ultra thin films.

Example 2

Figure 5:
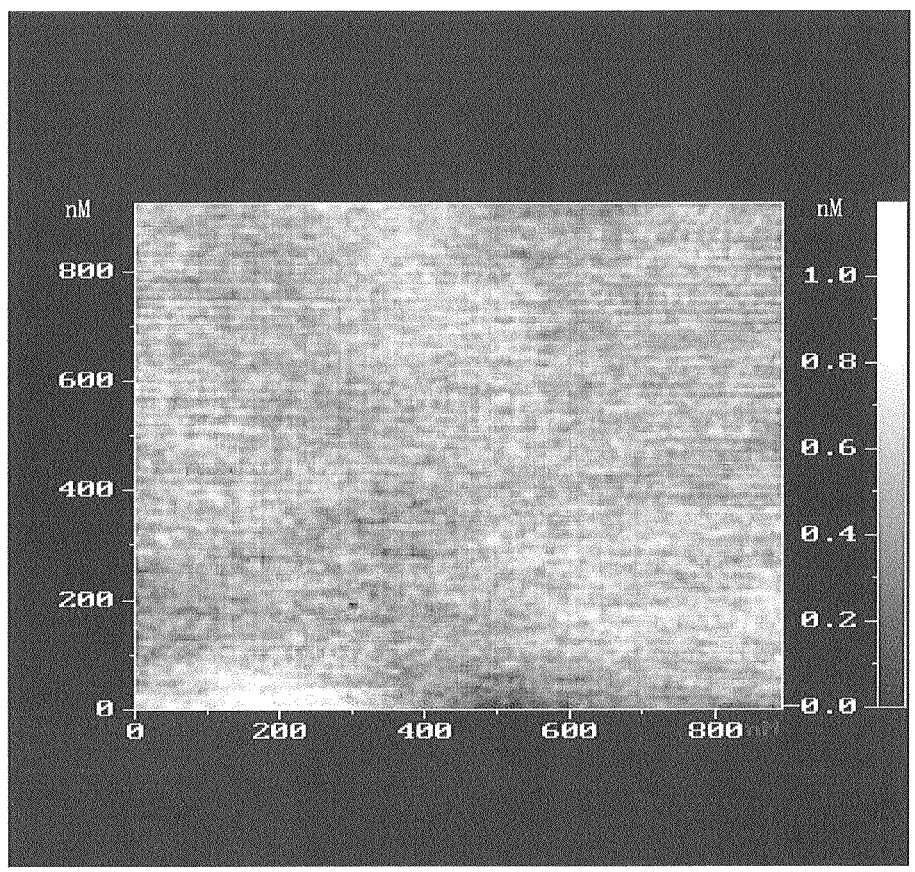
FIG. 5 is a conducting atomic force microscopy (C-AFM) image of the topographic structure of self-assembled quaternary ingredients on a silicon substrate, as described in Example 2. The regular network crystal thin film has a length of 800 nm, a width of 800 nm, and a height of 1 nm.
Figure 6:
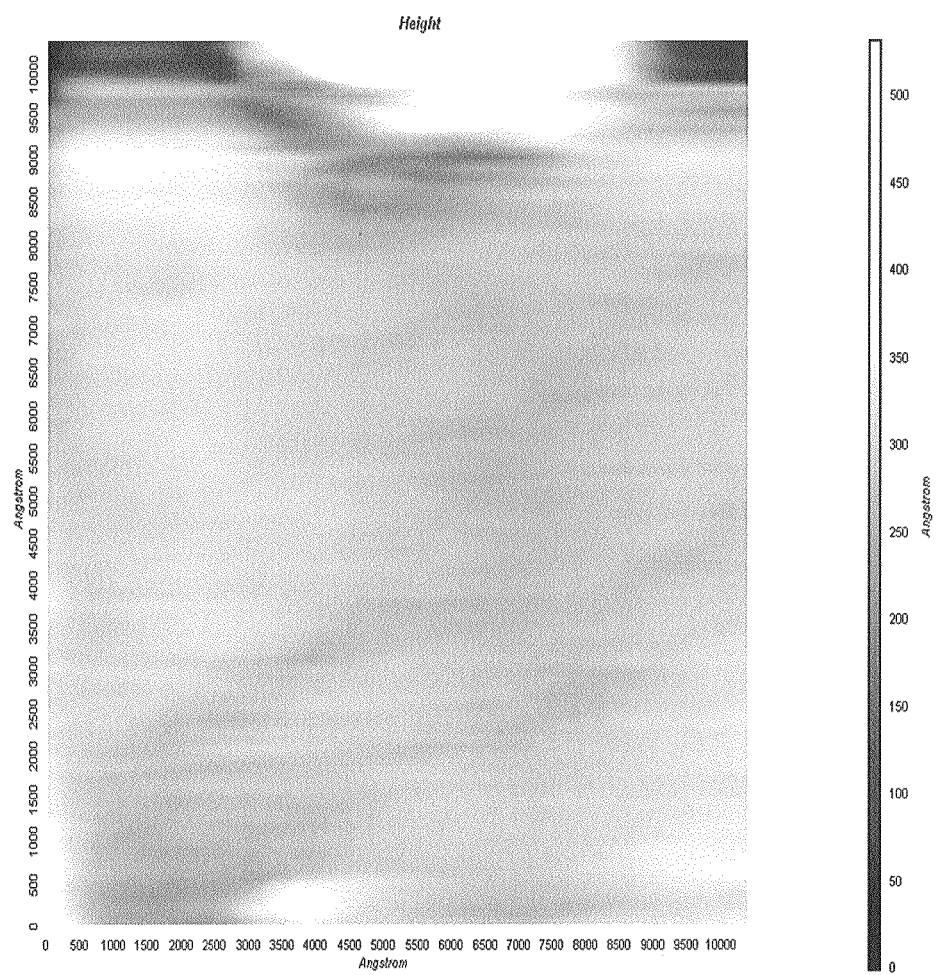
FIG. 6 is a conducting atomic force microscopy (C-AFM) image of the topographic structure of small, ternary self-assembled units (less than 10 nm) on a silicon substrate, as described in Example 3. The molecular nanometer crystal thin film has a length of 1000 nm, a width of 1000 nm, and a height of 50 nm.
Figure 7:
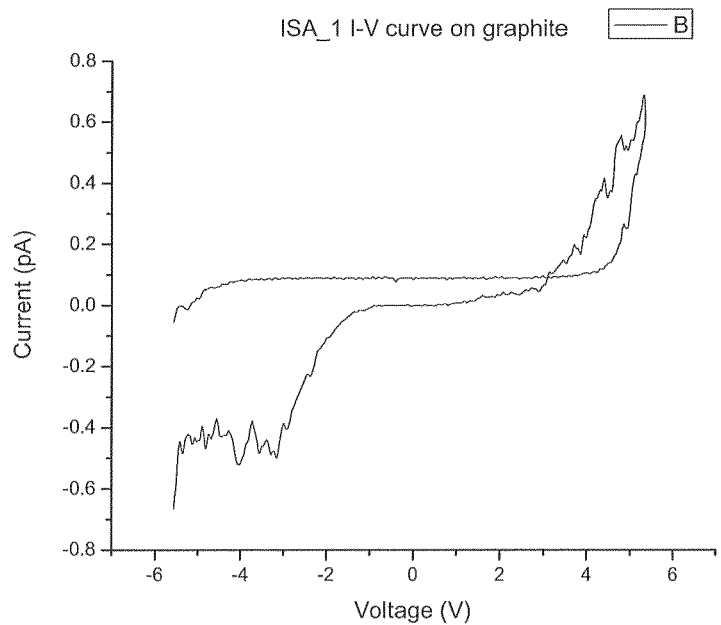
FIG. 7 is a conducting atomic force microscopy (C-AFM) probe tunneling current and bias voltage (I-V curves) corresponding to FIG. 1, indicating conductance of an insulator transition into a conductor as shown by a parallel level transient into ±7 pA tunneling currents with a higher current level and a lower current level for a digital logic 1/0 information memory.
Figure 8:
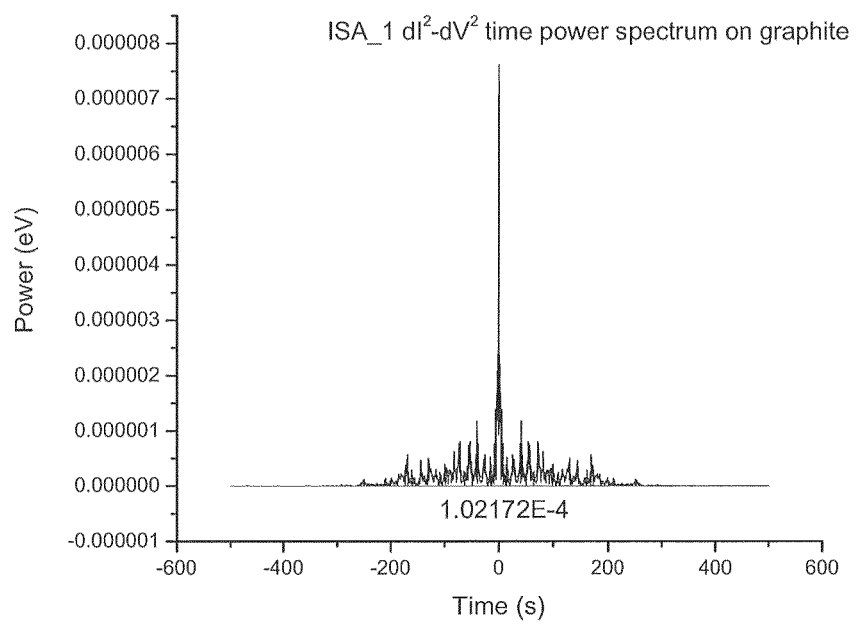
FIG. 8 is a fast Fourier transform of the data in FIG. 7, revealing lower power at 1-8 µeV levels.
Figure 9:
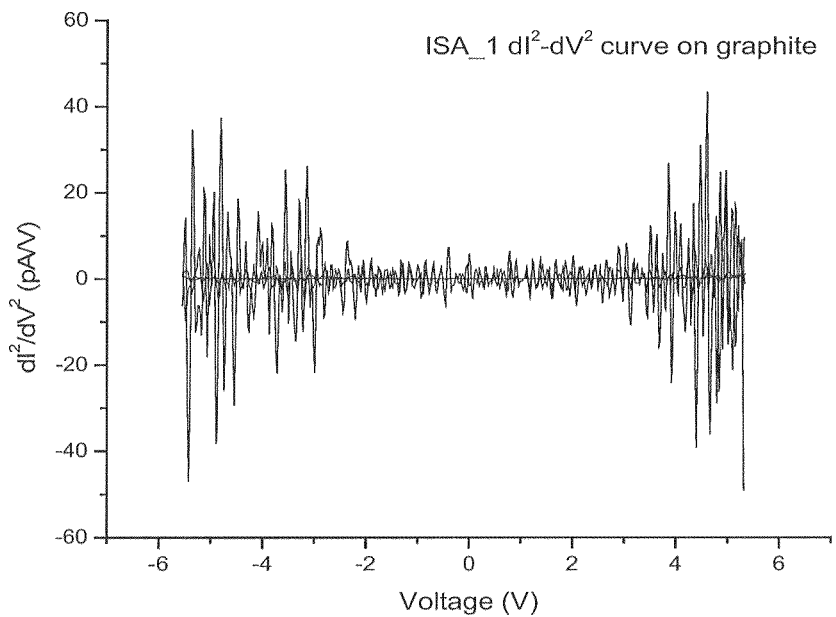
FIG. 9 is the non-zero 2nd derivative values of the I-V curves in FIG. 7, indicating inelastic tunneling.

Pharmaceutical liquids are prepared according to the pharmaceutical standards issued by the Ministry of Health in China. FIG. 5 is a C-AFM image of the 2:3:1:2 product obtained from Example 2.
i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. The pharmaceutical liquids are mixed in a molar ratio of 2:3:1:2 (verapamil:isoprenaline:superoxide dismutase:adenosine triphosphate) in 1 mL physiological buffer at room temperature. The solution is saved at −4° C. for application.
vi. 5 μL drops of the pharmaceutical liquid mixture are dropped on the graphite and silicon substrates according to the $L_9(3)^4$ test design, and saved at −4° C. for 12 hours to form size-controllable self-assembled nanomedicine crystals and/or ultra thin films.

Example 3

Pharmaceutical liquids are prepared according to the pharmaceutical standards issued by the Ministry of Health in China. FIGS. 1 and 6-10 depict images and data from the 0:1:1:1 product obtained in Example 3.
i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. The pharmaceutical liquids are mixed in a molar ratio of 0:1:1:1 (verapamil:isoprenaline:superoxide dismutase:adenosine triphosphate) in 1 mL physiological buffer at room temperature. The solution is saved at −4° C. for application.
vi. 5 μL drops of the pharmaceutical liquid mixture are dropped on the graphite and silicon substrates according to the $L_{16}(2)^{15}$ test design, and saved at −4° C. for 12 hours to form size-controllable self-assembled nanomedicine crystals and/or ultra thin films.

Example 4

Figure 2:
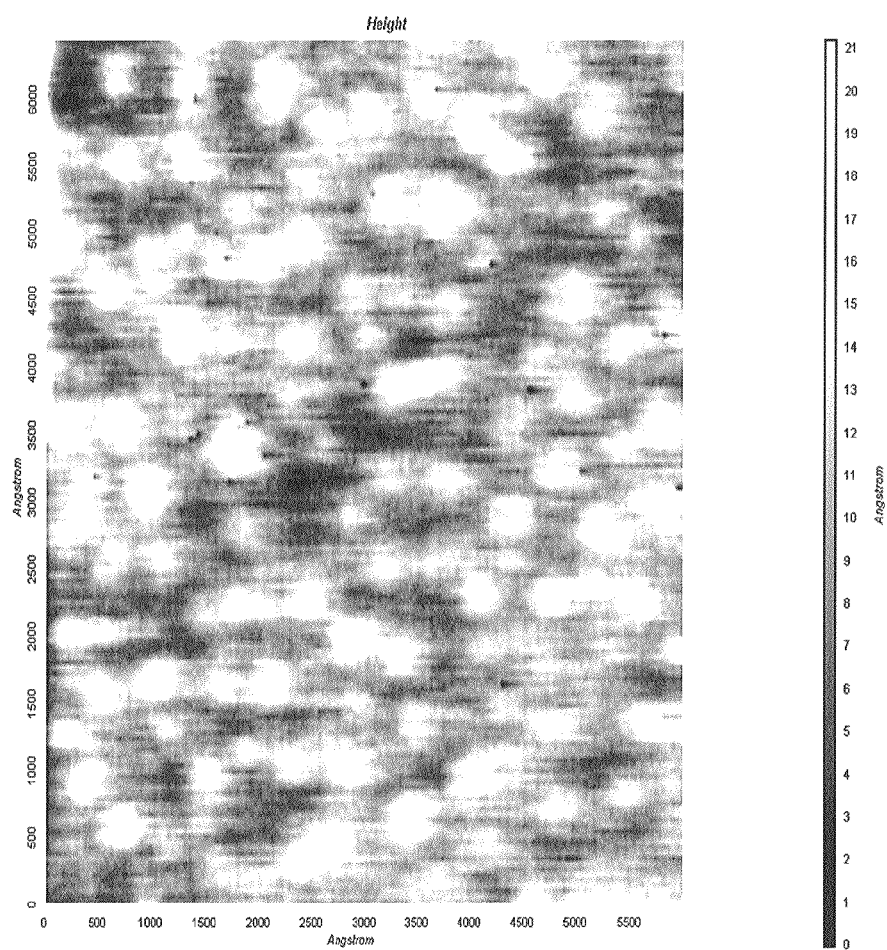
FIG. 2 is a conducting atomic force microscopy (C-AFM) image of the topographic structure of small, unitary self-assembled units (each unit 0.34 nm) on a silicon substrate. The geometrical size is a dot-like crystal cluster array with a length of 600 nm, a width of 550 nm, and a height of 2.1 nm.

Pharmaceutical liquids are prepared according to the pharmaceutical standards issued by the Ministry of Health in China. FIG. 2 depicts a C-AFM image of the 0:1:0:0 product obtained in Example 4.

i. A verapamil hydrochloride pharmaceutical liquid is prepared at a concentration of 2.5 mg/5 mL.
ii. An isoprenaline hydrochloride pharmaceutical liquid is prepared at a concentration of 2 mg/100 mL.
iii. A physiological buffer solution of superoxide dismutase is prepared at a concentration of 1 mg/2 mL.
iv. A physiological buffer solution of adenosine triphosphate is prepared at a concentration of 20 mg/3.3 mL.
v. The pharmaceutical liquids are mixed in a molar ratio of 0:1:0:0 (verapamil:isoprenaline:superoxide dismutase:adenosine triphosphate) in 1 mL physiological buffer at room temperature. The solution is saved at −4° C. for application.
vi. 5 μL drops of the pharmaceutical liquid mixture are dropped on the graphite and silicon substrates according to the $L_{16}(2)^{15}$ test design, and saved at −4° C. for 12 hours to form size-controllable self-assembled nanomedicine crystals and/or ultra thin films.

The invention claimed is:

1. A low power three-dimensional (3D) self-assembled conducting photoluminescent nanomedicine, comprising:
    3D unitary, binary, ternary, and quaternary nanomedicine crystals of isoprenaline, adenosine triphosphate, verapamil, and superoxide dismutase, in a $L_{16}(2)^{15}$ test protocol that includes four unitary groups, six binary groups, four ternary groups and one quaternary group at two levels of 0 and 1, and a $L_9(3)^4$ test protocol that includes nine quaternary groups at three levels of 1, 2 and 3,
    the 3D unitary, binary, ternary, and quaternary nanomedicine crystals disposed on a substrate of graphite and/or silicon,
    wherein the 3D unitary, binary, ternary, and quaternary nanomedicine crystals have a length from 400 nm to 1000 nm, a width from 400 nm to 1000 nm, and a height from 0.3 nm to 95 nm, and
    the low power three-dimensional (3D) self-assembled conducting photoluminescent nanomedicine has an inelastic electron tunneling property, a conducting property having a range of 1-8 μeV, and a photoluminescent property having a maximum photoluminescence intensity at 2000 absorbance units, a photoluminescence bandwidth covering 450-750 nm, and a central photoluminescence peak being located around 550 nm after subtraction of a background signal.

2. The low power 3D self-assembled conducting photoluminescent nanomedicine of claim 1, wherein a 3D topographic structure of the unitary, binary, ternary, and quaternary nanomedicine crystals are imaged by conducting atomic force microscopy (C-AFM), the inelastic electron tunneling interaction, the conducting property, the low power property at 1-8 μeV and the photoluminescent property are respectively shown by non-zero values in the $2^{nd}$ derivatives of current-voltage (I-V) curves of C-AFM, C-AFM I-V curves, the fast Fourier transformation of C-AFM I-V curves and a time-resolved laser micro-photoluminescence (PL) spectrum.

3. The low power 3D self-assembled conducting photoluminescent nanomedicine of claim 1 prepared by the unitary nanomedicine crystals having a molar ratio of (verapamil isoprenaline:superoxide dismutase:adenosine triphosphate) selected from the group consisting of (i) 1:0:0:0; (ii) 0:1:0:0; (iii) 0:0:1:0; (iv) 0:0:0:1, and combinations thereof, in the $L_{16}(2)^{13}$ test protocol.

4. The low power 3D self-assembled conducting photoluminescent nanomedicine of claim 1 prepared by the binary nanomedicine crystals having a molar ratio of (verapamil:isoprenaline:superoxide dismutase:adenosine triphosphate) selected from the group consisting of (i) 1:1:0:0; (ii) 1:0:1:0; (iii) 1:0:0:1; (iv) 0:1:1:0; (v) 0:1:0:1; (vi) 0:0:1:1, and combinations thereof, in the $L_{16}(2)^{15}$ test protocol.

5. The low power 3D self-assembled conducting photoluminescent nanomedicine of claim 1 prepared by the ternary nanomedicine crystals having a molar ratio of (verapamil:isoprenaline:superoxide dismutase:adenosine triphosphate) selected from the group consisting of (i) 1:1:1:0; (ii) 1:0:1:1; (iii) 1:1:0:1; (iv) 0:1:1:1, and combinations thereof in the $L_{16}(2)^{15}$ test protocol.

6. The low power 3D self-assembled conducting photoluminescent nanomedicine of claim 1 prepared by the quaternary nanomedicine crystals having a molar ratio of (verapamil:isoprenaline:superoxide dismutase:adenosine triphosphate) selected from the group consisting of (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; (ix) 3:3:2:1; and combinations thereof, in the $L_9(3)^4$ test protocol.

7. The low power 3D self-assembled conducting photoluminescent nanomedicine of claim 1 prepared by a unitary, binary, ternary, or quaternary process comprising:
    (a) preparing a solution of verapamil hydrochloride, a solution of isoprenaline hydrochloride, a physiological buffer solution of superoxide dismutase, and a physiological buffer solution of adenosine triphosphate;
    (b) mixing a selected molar ratio of the solutions chosen according to the $L_{16}(2)^{15}$ test protocol and the $L_9(3)^4$ test protocol in a physiological buffer solution;
    (c) dropping the mixture on the substrate to form a droplet of the mixture on the substrate; and
    (d) cooling the mixture on the substrate to −4° C. for 12 hours, during which time the mixture undergoes a phase transition from a liquid state to a solid state, to form size-controlled self-assembled conducting photoluminescent nanomedicine crystals on the substrate.

8. The low power 3D self-assembled conducting photoluminescent nanomedicine of claim 1, wherein,
    (a) the isoprenaline has a concentration range of about 15.1 pM to about 2.0 μM,
    (b) the adenosine triphosphate has a concentration range of about 1.0 nM to about 2.5 M,
    (c) the verapamil has a concentration range of about 2.0 nM to about 59.1 μM, and
    (d) the superoxide dismutase has a concentration range of about 15.1 pM to about 151 pM.

9. The low power 3D self-assembled conducting photoluminescent nanomedicine of claim 1, wherein the unitary, binary, ternary, and quaternary nanomedicine crystals have conducting photoluminescent properties, the unitary, binary, ternary, and quaternary nanomedicine crystals being bottom up self-assembled crystals on the substrate by a preparation process of using the inelastic electron tunneling that is demonstrated by conducting atomic force microscopy (C-AFM) current-voltage (I-V) curve measurements to show ±7 pA electron tunneling current and a non-zero value in $2^{nd}$ derivatives of I-V curves,
    wherein crystallized structures of the unitary, binary, ternary, and quaternary nanomedicine crystals, the conducting property, the low power property, and the photoluminescent property are respectively demonstrated by C-AFM topographic structure images, C-AFM I-V curves, fast Fourier transformations of C-AFM I-V curves, and low temperature laser micro-photoluminescence (PL) spectra, wherein the low power 3D self-assembled conducting photoluminescent nanomedicine comprises one or more of:
(a) the ternary crystals including a molecular crystal having a length of 400 nm, a width of 400 nm, and a height of 32 nm formed on the substrate by self-assembled units having a length of less than 10 nm;
(b) the unitary crystals including a dot-like unitary crystal cluster array having a length of 600 nm, a width of 550 nm, and a height of 2.1 nm formed on the substrate by self-assembled units having a length of 0.34 nm;
(c) the quaternary crystals including a tilted cross-bar-like crystal having a length of 1000 nm, a width of 1000 nm, and a height of 1.2 nm formed on the substrate by self-assembled units having a length of less than 10 nm;
(d) the unitary crystals including a non-symmetrical crystal having a length of 1000 nm, a width of 1000 nm, and a height of 95 nm formed on the substrate by self-assembled units having a length of 0.34 nm;
(e) the quaternary crystals including a regular network crystal having a length of 800 nm, a width of 800 nm, and a height of 1 nm formed on the substrate;
(f) the smallest crystal having a length of 4.5 nm, a width of 4.5 nm, and a height of 0.1 nm;
(g) the ternary crystals including a crystal having a length of 1000 nm, a width of 1000 nm, and a height of 50 nm; and
(h) a 3D crystal having a thickness from 2 angstroms to 2.5 nm, wherein the conducting property and the photoluminescence property are at the substrate.

10. The low power 3D self-assembled conducting photoluminescent nanomedicine of claim 9, wherein the inelastic electron tunneling is employed to make one or more unitary, binary, ternary, and quaternary interactions of crystallized 3D low power conducting photoluminescent nanomedicine on the substrate, from droplets selected from the group consisting of:
(a) the isoprenaline;
(b) the adenosine triphosphate;
(c) the verapamil; and
(d) the superoxide dismutase;
according to the $L_{16}(2)^{15}$ test protocol and the $L_9(3)^4$ test protocol.

11. The low power 3D self-assembled conducting photoluminescent nanomedicine of claim 9, wherein the isoprenaline is on the substrate.

12. The low power 3D self-assembled conducting photoluminescent nanomedicine of claim 9, wherein the adenosine triphosphate is on the substrate.

13. The low power 3D self-assembled conducting photoluminescent nanomedicine of claim 9, wherein the verapamil is on the substrate.

14. The low power 3D self-assembled conducting photoluminescent nanomedicine of claim 9, wherein the superoxide dismutase is on the substrate.

15. The low power 3D self-assembled conducting photoluminescent nanomedicine of claim 9, wherein the unitary nanomedicine crystals having conducting and photoluminescent properties are self-assembled and selected from the group of molar ratios of (verapamil isoprenaline:superoxide dismutase:adenosine triphosphate) consisting of (i) 1:0:0:0; (ii) 0:1:0:0; (iii) 0:0:1:0; and (iv) 0:0:0:1.

16. The low power 3D self-assembled conducting photoluminescent nanomedicine of claim 9, wherein the binary nanomedicine crystals having conducting and photoluminescent properties are self-assembled and selected from the group of molar ratios of (verapamil:isoprenaline:superoxide dismutase:adenosine triphosphate) consisting of (i) 1:1:0:0; (ii) 1:0:1:0; (iii) 1:0:0:1; (iv) 0:1:1:0; (v) 0:1:0:1; and (vi) 0:0:1:1.

17. The low power 3D self-assembled conducting photoluminescent nanomedicine of claim 9, wherein the ternary nanomedicine crystals having conducting and photoluminescent properties are self-assembled and selected from the group of molar ratios of (verapamil:isoprenaline:superoxide dismutase:adenosine triphosphate) consisting of (i) 1:1:1:0; (ii) 1:1:0:1; (iii) 1:0:1:1; and (iv) 0:1:1:1.

18. The low power 3D self-assembled conducting photoluminescent nanomedicine of claim 9, wherein the quaternary nanomedicine crystals having conducting and photoluminescent properties are self-assembled and selected from the group of molar ratios of (verapamil isoprenaline:superoxide dismutase:adenosine triphosphate) consisting of (i) 1:1:1:1; (ii) 1:2:2:2; (iii) 1:3:3:3; (iv) 2:1:2:3; (v) 2:2:3:1; (vi) 2:3:1:2; (vii) 3:1:3:2; (viii) 3:2:1:3; and (ix) 3:3:2:1.

19. A method of providing for self-assembly of the 3D unitary, binary, ternary, and quaternary nanomedicine crystals for making the low power 3D self-assembled conducting photoluminescent nanomedicine of claim 1, comprising:
(a) forming a droplet of a solution comprising one or more ingredients selected from the group consisting of verapamil, isoprenaline, superoxide dismutase, and adenosine triphosphate, on the substrate;
(b) cooling the substrate to a temperature of about −4° C.; and
(c) allowing the droplet to cool for 12 hours such that the ingredients in the droplet undergo a phase transition and self-assemble to form a crystal.

20. The method of claim 19, wherein the solution comprises a concentration of the verapamil being in a range from about 2 nM to about 59.1 μM, a concentration of the isoprenaline being in a range from about 15 pM to about 2 μM, a concentration of the adenosine triphosphate being in a range from about 1 nM to about 2.5 M, and a concentration of the superoxide dismutase being in a range from about 15.1 pM to about 151 pM.

* * * * *